United States Patent
Sunley et al.

(10) Patent No.: US 12,043,591 B2
(45) Date of Patent: *Jul. 23, 2024

(54) FISCHER-TROPSCH PROCESS

(71) Applicant: BP p.l.c., London (GB)

(72) Inventors: John Glenn Sunley, Hull East (GB); Alexander James Paterson, Hull East (GB)

(73) Assignee: BP P.L.C., London (GB)

( * ) Notice: Subject to any disclaimer, the term of this patent is extended or adjusted under 35 U.S.C. 154(b) by 485 days.

This patent is subject to a terminal disclaimer.

(21) Appl. No.: 17/280,542

(22) PCT Filed: Sep. 26, 2019

(86) PCT No.: PCT/EP2019/076034
§ 371 (c)(1),
(2) Date: Mar. 26, 2021

(87) PCT Pub. No.: WO2020/064929
PCT Pub. Date: Apr. 2, 2020

(65) Prior Publication Data
US 2022/0220053 A1  Jul. 14, 2022

(30) Foreign Application Priority Data

Sep. 28, 2018 (EP) .................... 18197717

(51) Int. Cl.
| | | |
|---|---|---|
| *C07C 29/156* | (2006.01) | |
| *B01J 21/06* | (2006.01) | |
| *B01J 23/889* | (2006.01) | |
| *C07C 1/04* | (2006.01) | |

(52) U.S. Cl.
CPC .......... *C07C 29/156* (2013.01); *B01J 21/063* (2013.01); *B01J 23/8892* (2013.01); *C07C 1/0435* (2013.01); *C07C 2521/06* (2013.01); *C07C 2523/75* (2013.01); *C07C 2523/889* (2013.01)

(58) Field of Classification Search
CPC . C07C 29/156; C07C 1/0435; C07C 2521/06; C07C 2523/75; C07C 2523/889; C07C 31/04; C10G 2/32; C10G 2/50
See application file for complete search history.

(56) References Cited

U.S. PATENT DOCUMENTS

| | | |
|---|---|---|
| 4,291,126 A | 9/1981 | Sugier et al. |
| 4,791,141 A | 12/1988 | Chaumette et al. |
| 5,958,985 A | 9/1999 | Geerlings et al. |
| 5,981,608 A | 11/1999 | Geerlings et al. |

FOREIGN PATENT DOCUMENTS

WO   2018/146277 A1   8/2018

OTHER PUBLICATIONS

Morales (Synthesis and characterization of titania-supported cobalt Fischer-Tropsch catalysts promoted with manganese oxide, 2006, pp. 45-64).*
Jinping et al., CN104959148A (machine translation 2015).*
International Search Report and Written Opinion in International Patent Application No. PCT/EP2019/076034, dated Dec. 18, 2019.
De Jong et al. "Cobalt Particle Size Effects in the Fischer-Tropsch Reaction Studied with Carbon Nanofiber Supported Catalysts." J. Am. Chem. Soc. 2006, vol. 128, No. 12, p. 3956-3964.

* cited by examiner

*Primary Examiner* — Jafar F Parsa
(74) *Attorney, Agent, or Firm* — McDonnell Boehnen Hulbert & Berghoff LLP

(57) ABSTRACT

A process for the preparation of a composition comprising oxygenates and hydrocarbons by means of a Fischer-Tropsch synthesis reaction, said process comprising contacting a mixture of hydrogen, carbon monoxide, and carbon dioxide gases with a supported Co—Mn Fischer-Tropsch synthesis catalyst, wherein the supported synthesis catalyst comprises at least 2.5 wt % of manganese, on an elemental basis, based on the total weight of the supported synthesis catalyst; the weight ratio of manganese to cobalt, on an elemental basis, is 0.2 or greater; and, wherein carbon dioxide is present in the Fischer-Tropsch synthesis reaction is at least 5% v/v.

21 Claims, No Drawings

FISCHER-TROPSCH PROCESS

This application is a national stage application under 35 U.S.C. § 371 of International Application No. PCT/EP2019/076034, filed Sep. 26, 2019, which claims priority to European Patent Application No. 18197717.4, filed Sep. 28, 2018.

This invention relates to a Fischer-Tropsch process for the preparation of oxygenates and hydrocarbons employing a supported Fischer-Tropsch synthesis catalyst containing both cobalt and manganese, wherein carbon dioxide is included in the feed to the Fischer-Tropsch process. Also provided is the use of carbon dioxide in a Fischer-Tropsch process employing a supported cobalt manganese (Co—Mn) Fischer-Tropsch synthesis catalyst for increasing the selectivity of a Fischer-Tropsch process for the production of oxygenates, particularly alcohols.

The conversion of synthesis gas into hydrocarbons by the Fischer-Tropsch process has been known for many years. The growing importance of alternative energy sources has seen renewed interest in the Fischer-Tropsch process as one of the more attractive direct and environmentally acceptable routes to high quality transportation fuels and lubricants.

Many metals, for example cobalt, nickel, iron, molybdenum, tungsten, thorium, ruthenium, rhenium and platinum are known to be catalytically active, either alone or in combination, in the conversion of synthesis gas into hydrocarbons and oxygenated derivatives thereof. Of the aforesaid metals, cobalt, nickel and iron have been studied most extensively. Generally, the metals are used in combination with a support material, of which the most common are alumina, silica and carbon.

In the preparation of supported cobalt-containing Fischer-Tropsch synthesis catalysts, a solid support material is typically impregnated with a cobalt-containing compound, which may for instance be an organometallic or inorganic compound (e.g. $Co(NO_3)_2 \cdot 6H_2O$), by contacting with a solution of the compound. The particular form of cobalt-containing compound is generally selected for its ability to form a cobalt oxide (for instance, CoO, $Co_2O_3$ or $Co_3O_4$) following a subsequent calcination/oxidation step. Following generation of the supported cobalt oxide, a reduction step is necessary in order to form the pure cobalt metal as the active catalytic species. Thus, the reduction step is also commonly referred to as an activation step.

During calcination, cobalt oxides form crystallites on the support material, and the properties of such crystallites, such as dispersion, particle size and reduction degree, are known to have an effect on the activity and selectivity of the catalyst in Fischer-Tropsch processes. For example, de Jong et al. (J. Am. Chem. Soc., 128, 2006, 3956-3964) showed that for optimal activity and selectivity for $C_{5+}$ hydrocarbons, cobalt metal particles in the active catalyst having sizes of around 6 to 8 nm are particularly beneficial.

Typically, the principal focus in adapting Fischer-Tropsch synthesis catalysts is for improving activity and selectivity for $C_{5+}$ hydrocarbons (paraffins). Nevertheless, alcohols and liquid hydrocarbons are also desirable products of the Fisher-Tropsch process and process conditions and synthesis catalyst design may be tailored to favour the production of those materials.

Hydrocarbon fuel deriving from Fischer-Tropsch processes are better able to meet increasingly stringent environmental regulations, as compared with conventional refinery fuel, since hydrocarbon fuel obtainable from the Fischer-Tropsch process is essentially free of sulfur and aromatic compounds and has a low nitrogen content. This may result in much lower emissions of pollutants such as CO, $CO_2$, $SO_2$, and $NO_x$, as well as little or no particulate emissions. Meanwhile, alcohols deriving from Fischer-Tropsch processes have a higher octane rating than hydrocarbons and thus can burn more completely, thereby reducing the environmental impact of such a fuel. Alcohols obtained from a Fischer-Tropsch reaction may also be advantageously used as reagents in other processes, such as polymerisation, surfactants, and cosmetics, a particular benefit being the purity of the alcohols obtainable by a Fischer-Tropsch process. Long-chained alcohols are also particularly useful as lubricant components, or precursors thereof. Linear alpha olefins (LAO) and linear alcohols have significant value as a basis for fine chemicals, lubricants and plasticisers/polymers.

de Jong et al. discussed above does not focus on the impact of cobalt particle size on the activity and selectivity for producing alcohols or liquid hydrocarbons. FIG. 9 of de Jong et al. indicates that methane selectivity is higher where the cobalt particle size is less than 5 nm and that selectivity for methane remains relatively constant for increases in cobalt particle size above 5 nm for the Fischer-Tropsch process conditions tested.

It would be desirable to provide a means for improving the activity and selectivity of a Fischer-Tropsch process for the production of alcohols and liquid hydrocarbons, in particularly alcohols and olefins, and especially alcohols. The present invention is based on the discovery of certain benefits of utilizing a Fischer-Tropsch synthesis catalyst comprising a combination of cobalt and manganese, at a particular weight ratio, in increasing the activity and selectivity of the Fischer-Tropsch reaction for the preparation of alcohols and liquid hydrocarbons.

U.S. Pat. No. 5,981,608 describes the use of a supported catalyst comprising cobalt and manganese, where the atomic ratio of cobalt to manganese in the catalyst is at least 12:1, for use in improving the $C_{5+}$ hydrocarbon selectivity of a Fischer-Tropsch process. Similarly, U.S. Pat. No. 5,958,985 describes the use of a catalyst comprising cobalt and manganese in a cobalt/manganese molar ratio of from 13:1 to 9:1 for improving the $C_{5+}$ hydrocarbon selectivity of a Fischer-Tropsch process. However, neither of these documents describes how to modify the catalyst composition for improving activity and selectivity of a Fischer-Tropsch process for the production of alcohols and liquid hydrocarbons (below approximately $C_{24}$).

It has been surprisingly found that the combination of the use of carbon dioxide in the gaseous feed, and the use of a supported catalyst comprising manganese and cobalt, present at a weight ratio of manganese to cobalt, on an elemental basis, of from 0.2 or greater, and comprising at least 2.5 wt. % of manganese, on an elemental basis, is particularly useful in improving activity and selectivity of a Fischer-Tropsch process for the production of oxygenates, in particularly alcohols.

In a first aspect, the present invention provides a process for the preparation of a composition comprising oxygenates and hydrocarbons by means of a Fischer-Tropsch synthesis reaction, said process comprising contacting a mixture of hydrogen, carbon monoxide, and carbon dioxide gases with a supported Co—Mn Fischer-Tropsch synthesis catalyst, wherein the supported synthesis catalyst comprises at least 2.5 wt % of manganese, on an elemental basis, based on the total weight of the supported synthesis catalyst; the weight ratio of manganese to cobalt, on an elemental basis, is 0.2 or greater; and, wherein the amount of carbon dioxide present in the Fischer-Tropsch synthesis reaction is at least 5% v/v.

In another aspect of the present invention, there is provided the use of carbon dioxide in the feed to a Fischer-Tropsch synthesis reaction using a supported Co—Mn Fischer-Tropsch synthesis catalyst, wherein the supported synthesis catalyst comprises at least 2.5 wt % of manganese, on an elemental basis, based on the total weight of the supported synthesis catalyst; the weight ratio of manganese to cobalt, on an elemental basis, is 0.2 or greater, for increasing the selectivity of the Fischer-Tropsch process for the production of alcohols.

The present invention provides a process for converting a mixture of hydrogen, carbon monoxide, and carbon dioxide gases to a composition comprising oxygenates, in particularly alcohols, and hydrocarbons by means of a Fischer-Tropsch synthesis reaction, said process comprising contacting a mixture of hydrogen and carbon monoxide gases, preferably in the form of synthesis gas mixture, with a supported Co—Mn Fischer-Tropsch synthesis catalyst. The product composition produced by the Fischer-Tropsch synthesis reaction will also comprise other components, such as waxes as well as other oxygenates, however, the process of the present invention exhibits an increase in selectivity to alcohols and liquid hydrocarbons compared to conventional Fischer-Tropsch synthesis reactions using a cobalt-based catalyst.

The hydrocarbons produced by the process of the present invention comprise a significant proportion of olefins. In some or all embodiments, the hydrocarbons comprise at least 1 wt. % olefins, for example at least 2 wt. % olefins or at least 3 wt. % olefins, such as at least 5 wt. % olefins, at least 10 wt. % olefins, or at least 20 wt. % olefins; preferably, the olefins will comprise linear alpha olefins, more preferably the olefins will comprise at least 50 wt. % linear alpha olefins, such as at least 70 wt. % linear alpha olefins.

The term "oxygenates" used herein comprises a range of oxygenates which may be produced by a Fischer-Tropsch synthesis reaction. Typically, the oxygenates produced in the process of the present invention will comprise a significant proportion of alcohols, for example, the oxygenates produced in the process of the present invention will comprise the olefins will comprise at least 50 wt. % alcohols, such as at least 80 wt. % alcohols, based on the total amount of oxygenates produced.

The term "alcohols" used herein in reference to the products of the Fischer-Tropsch reaction refers to an alcohol having any number of carbon atoms. The alcohols are typically acyclic and may be straight- or branched-chain, preferably straight-chain. In some or all embodiments, the alcohols will comprise at least 50 wt. % linear alpha alcohols, such as at least 70 wt. % linear alpha alcohols or at least 80 wt. % linear alpha alcohols.

In some embodiments, the alcohols prepared by the process of the present invention include a major proportion (above 50 wt. %) of short-chain length $C_1$ to $C_4$ alcohols. In other embodiments, the alcohols prepared by the process of the present invention include a major proportion (above 50 wt. %) of medium-chain length $C_5$ to $C_9$ alcohols. In other embodiments, the alcohols prepared by the process of the present invention include a major proportion (above 50 wt. %) long-chain length $C_{10}$ to $C_{25}$ alcohols. The amount of alcohols produced by the Fischer-Tropsch reaction, and the relative proportion of short, medium and long chain may be determined by on-line GC mass spectrometry or other suitable technique.

In some or all embodiments, at least 15 wt. % of the products having a carbon chain length in the range of from $C_8$ to $C_{24}$ are alcohols. In some or all embodiments, at least 20 wt. % of the products having a carbon chain length in the range of from $C_8$ to $C_{24}$ are alcohols.

In some or all embodiments, the process of the present invention has a combined selectivity for alcohols and olefins of at least 15%, for example at least 20%, or even at least 40%. In some or all embodiments, the process of the present invention provides a product composition wherein in the $C_8$ to $C_{24}$ carbon chain length range, the combined selectivity for alcohols and olefins is at least 15%, for example at least 20%, or even at least 40%.

In some or all embodiments, the process of the present invention has a selectivity for alcohols of at least 15%, for example at least 20%, or even at least 40%. In some or all embodiments, the process of the present invention provides a product composition wherein in the $C_8$ to $C_{24}$ carbon chain length range, the selectivity for alcohols is at least 15%, for example at least 20%, or even at least 40%.

In some or all embodiments, the process of the present invention has a combined alcohol and olefin productivity of at least 50 g/L·h (grams per litre of catalyst per hour), for example at least 70 g/L·h, or even at least 90 g/L·h. In some or all embodiments, the process of the present invention provides a product composition wherein in the C8 to C24 carbon chain length range, the a combined alcohol and olefin productivity is at least 50 g/L·h, for example at least 70 g/L·h, or even at least 90 g/L·h.

In some or all embodiments, the process of the present invention has an alcohol productivity of at least 50 g/L·h, for example at least 70 g/L·h, or even at least 90 g/L·h. In some or all embodiments, the process of the present invention provides a product composition wherein in the C8 to C24 carbon chain length range, the alcohol productivity is at least 50 g/L·h, for example at least 70 g/L·h, or even at least 90 g/L·h.

The combination of the total amount of manganese and the weight ratio of manganese to cobalt has been found to be important to the process of the present invention. In particular, the use of a catalyst having this combination of total amount of manganese and the weight ratio of manganese to cobalt in a Fischer-Tropsch synthesis as described, it have been found to produce a product composition having a significant proportion of oxygenates, and, advantageously, for each carbon chain length having from 8 to 24 carbon atoms, at least 15%, for example at least 20%, of each carbon chain length is an oxygenate; in some or all embodiments, at least 15%, for example at least 20%, of each carbon chain length is an alcohol. In some or all embodiments, at least 15 wt. % of the $C_8$ to $C_{24}$ carbon chain length molecules are oxygenates, for example at least 20 wt. % or even at least 30 wt. % of the $C_8$ to $C_{24}$ carbon chain length molecules are oxygenates. In some or all embodiments, at least 15 wt. % of the $C_8$ to $C_{24}$ carbon chain length molecules are alcohols, for example at least 20 wt. % or even at least 30 wt. % of the $C_8$ to $C_{24}$ carbon chain length molecules are alcohols.

Without wishing to be bound by theory, it is believed that preparing a catalyst which comprises at least 2.5 wt. % manganese and a manganese to cobalt weight ratio, on an elemental basis, of at least 0.2, by impregnation, the cobalt oxide crystallite ($Co_3O_4$) sizes in the resulting supported Co—Mn Fischer-Tropsch synthesis catalyst are of a particle size which may give rise to, or contribute to, benefits when the catalyst is utilized in a Fischer-Tropsch reaction. In particular, the cobalt oxide crystallite ($Co_3O_4$) particle sizes resulting from the combination of total amount of manganese and the weight ratio manganese to cobalt weight ratio employed in the present invention have been found to be less than 100 Angstroms (10 nm), for example less than 80 Angstroms (8 nm), preferably less than 60 Angstroms (6 nm), such as less than 40 Angstroms (4 nm) or less than 35 Angstroms (3.5 nm). This crystallite size is of the same order, and also notably smaller than the cobalt particle size indicated as being particularly preferred for optimal activity and selectivity for $C_{5+}$ hydrocarbons in de Jong et al., discussed hereinbefore, namely 6 to 8 nm. Nevertheless, once the Co—Mn Fischer-Tropsch synthesis catalyst is activated and utilized in a Fischer-Tropsch reaction, productivity and selectivity for alcohols is notably enhanced over cobalt-containing synthesis catalysts comprising no manganese, or an insufficient amount of manganese having regard to the criteria of the present invention. Additionally, without being bound by theory, it is believed that the productivity and selectivity for olefins is notably enhanced over cobalt-containing synthesis catalysts comprising no manganese, or an insufficient amount of manganese having regard to the criteria of the present invention.

Without being bound by any particular theory, it is believed that the presence of manganese contributes to surface effects on the solid support which influences cobalt oxide crystallite development and dispersivity at the surface. This may derive from the mobility of cobalt-containing precursor compound(s) which are applied to the support material during catalyst preparation, for instance suspended or dissolved in an impregnation solution, whilst in the presence of manganese-containing precursor compound(s). Thus, the catalyst of the present invention preferably involves cobalt-containing precursor compound(s) and manganese-containing precursor compound(s) being applied to a support material such that they form a mobile admixture at the surface of the support during its preparation.

In some or all embodiments, the weight ratio of manganese to cobalt present in the supported Co—Mn Fischer-Tropsch synthesis catalyst, on an elemental basis, is from 0.2 to 3.0; specific examples of weight ratios of manganese to cobalt include from 0.2 to 2.0, from 0.2 to 1.5, from 0.2 to 1.0, from 0.2 to 0.8, from 0.3 to 2.0, from 0.3 to 1.5, from 0.3 to 1.0, and from 0.3 to 0.8. Typically, the weight ratio of manganese to cobalt present in the supported Co—Mn Fischer-Tropsch synthesis catalyst, on an elemental basis, is at least 0.3, more typically at least 0.3, and at most 1.5, more typically at most 1.0.

The benefits of the manganese loading and the weight ratio of elemental manganese to elemental cobalt according to the invention may be observed over a large range of concentrations of cobalt and manganese in the supported synthesis catalyst. However, in some or all embodiments, the supported synthesis catalyst comprises manganese, on an elemental basis, in an amount of at least 3.0 wt. % based on the total weight of the supported synthesis catalyst.

In preferred embodiments, the supported Co—Mn Fischer-Tropsch synthesis catalyst contains from 5 wt. % to 35 wt. % of cobalt, more preferably from 7.5 wt % to 25 wt % of cobalt, even more preferably from 10 to 20 wt. % of cobalt, on an elemental basis, based on the total weight of the supported synthesis catalyst.

In other preferred embodiments, the supported Co—Mn Fischer-Tropsch synthesis catalyst contains from 2.5 wt. % to 15 wt. % of manganese, preferably from 3.0 wt % to 12.5 wt % of manganese, for example from 3.0 to 10 wt. % of manganese, or even 4.0 to 8.0 wt. % of manganese, on an elemental basis, based on the total weight of the supported synthesis catalyst.

In some or all embodiments, the supported Co—Mn Fischer-Tropsch synthesis catalyst comprises less than 0.1 wt. % of copper, preferably less than 0.01 wt. % of copper, on an elemental basis, based on the total weight of the supported synthesis catalyst; more preferably, the supported Co—Mn Fischer-Tropsch synthesis catalyst does not contain copper.

In some or all embodiments, the supported Co—Mn Fischer-Tropsch synthesis catalyst comprises less than 0.1 wt. % of sodium, preferably less than 0.01 wt. % of sodium, on an elemental basis, based on the total weight of the supported synthesis catalyst; more preferably, the supported Co—Mn Fischer-Tropsch synthesis catalyst does not contain sodium.

The supported Co—Mn Fischer-Tropsch synthesis catalyst having a weight ratio of manganese to cobalt as described hereinbefore has been found to be particularly useful in Fischer-Tropsch reaction for providing selectivity for the production of alcohols, in particularly when the temperature of the Fischer-Tropsch reaction is in the range from 150 to 350° C., more preferably from 180 to 300° C., and most preferably from 200 to 260° C.

In preferred embodiments, the pressure of the Fischer-Tropsch reaction is in the range from 1 to 120 bar (from 0.1 to 10.2 MPa), such as from 5 to 100 bar (from 0.5 to 10 MPa), preferably from 10 to 100 bar (from 1 to 10 MPa), more preferably from 10 to 80 bar (from 1 to 8 MPa), more preferably from 10 to 60 bar (from 1 to 6 MPa), for example from 15 to 50 bar (from 1.5 to 5 MPa) or from 20 to 45 bar (from 2 to 4.5 MPa).

The supported Co—Mn Fischer-Tropsch synthesis catalyst used in accordance with the present invention may be prepared by any suitable method which is able to provide the required manganese to cobalt weight ratio and the required concentration of manganese on the supported. Preferably, the supported Co—Mn Fischer-Tropsch synthesis catalyst used in accordance with the present invention is prepared by a process in which the cobalt and the manganese are impregnated on to the support material.

A suitable impregnation method, for example, comprises impregnating a support material with cobalt-containing compound, which is thermally decomposable to the oxide form, and a manganese-containing compound. Impregnation of the support material with the cobalt-containing compound and the manganese-containing compound may be achieved by any suitable method of which the skilled person is aware, for instance by vacuum impregnation, incipient wetness or immersion in excess liquid.

The incipient wetness technique is so-called because it requires that the volume of impregnating solution be predetermined so as to provide the minimum volume of solution necessary to just wet the entire surface of the support, with no excess liquid. The excess solution technique as the name implies, requires an excess of the impregnating solution, the solvent being thereafter removed, usually by evaporation.

The support material may be in the form of a powder, granulate, shaped particle, such as a preformed sphere or microsphere, or extrudate. Reference herein to a powder or granulate of a support material is understood to refer to free flowing particles of a support material or particles of support material that have undergone granulation and/or sieving to be a particular shape (e.g. spherical) and size range. Reference herein to an "extrudate" is intended to mean a support material that has undergone an extrusion step and therefore may be shaped. In the context of the present invention, the powder or granulate is in a form which is suitable for impregnation with a solution of cobalt-containing compound and manganese-containing compound, and subsequent extrusion or forming into other shaped particles.

The support material used in the present invention may be any support suitable for use in a Fischer-Tropsch synthesis catalyst. Preferably, the support material used will comprises a material selected from titania, zinc oxide, alumina, zirconia, and ceria. In some or all embodiments, the support material is selected from the group consisting of ceria, zinc oxide, alumina, zirconia, titania, and mixtures thereof; preferably selected from titania and zinc oxide; more preferably selected from titania or mixtures containing titania. An example of a preferred titania support material particulate is titania powder, e.g. P25 Degussa.

It will be understood that the support material may be in any form provided it is suitable for use as a support for a Fischer-Tropsch synthesis catalyst and also preferably where the support material has not been previously impregnated with sources of metal other than cobalt and/or manganese which may have a deleterious effect on the performance of the active catalyst and may interfere with the benefits of the invention. Thus, whilst support material that has been previously loaded with cobalt and/or manganese metal, or precursors thereof, may be used in accordance with the invention, other pre-treatments providing sources of other metals are preferably to be avoided.

Preferred support materials are substantially free of extraneous components which might adversely affect the catalytic activity of the system. Thus, preferred support materials are at least 95% w/w pure, more preferably at least 98% w/w pure and most preferably at least 99% w/w pure. Impurities preferably amount to less than 1% w/w, more preferably less than 0.50% w/w and most preferably less than 0.25% w/w. The pore volume of the support is preferably more than 0.150 ml/g and preferably more than 0.30 ml/g. The average pore radius (prior to impregnation) of the support material is 10 to 500 Å, preferably 15 to 100 Å, more preferably 20 to 80 Å and most preferably 25 to 60 Å. The BET surface area is suitably from 2 to 1000 $m^2$ g, preferably from 10 to 600 $m^2/g$, more preferably from 15 to 100 $m^2/g$, and most preferably 30 to 60 $m^2/g$.

The BET surface area, pore volume, pore size distribution and average pore radius may be determined from the nitrogen adsorption isotherm determined at 77K using a Micromeritics TRISTAR 3000 static volumetric adsorption analyser. A procedure which may be used is an application of British Standard methods BS4359:Part 1:1984 'Recommendations for gas adsorption (BET) methods' and BS7591: Part 2:1992, 'Porosity and pore size distribution of materials'—Method of evaluation by gas adsorption. The resulting data may be reduced using the BET method (over the pressure range 0.05-0.20 P/Po) and the Barrett, Joyner & Halenda (BJH) method (for pore diameters of 20-1000 Å) to yield the surface area and pore size distribution respectively.

Suitable references for the above data reduction methods are Brunauer, S, Emmett, P H, & Teller, E, J. Amer. Chem. Soc. 60, 309, (1938) and Barrett, E P, Joyner, L G & Halenda P P, J. Am Chem. Soc., 1951 73 373-380.

When in the form of a powder, the median particle size diameter (d50) is preferably less than 50 μm, more preferably less than 25 μm. When the support material is in the form of a granulate, the median particle size diameter (d50) is preferably from 300 to 600 μm. Particle size diameter (d50) may suitably be determined by means of a particle size analyser (e.g. Microtrac 53500 Particle size analyser).

It is known to be beneficial to perform Fischer-Tropsch catalysis with a shaped particle, such as an extrudate, particularly in the case of fixed catalyst bed reactor systems. It is, for instance, known that, for a given shape of catalyst particles, a reduction in the size of the catalyst particles in a fixed bed gives rise to a corresponding increase in pressure drop through the bed. Thus, the relatively large shaped particles cause less of a pressure drop through the catalyst bed in the reactor compared to the corresponding powdered or granulated supported catalyst. Shaped particles, such as extrudates, also generally have greater strength and experience less attrition, which is of particular value in fixed bed arrangements where bulk crush strength must be very high.

Reference herein to "impregnation" or "impregnating" is intended to refer to contact of the support material with a solution, or solutions, of a cobalt-containing compound and a manganese-containing compound, before drying in order to achieve precipitation of the cobalt-containing compound and the manganese-containing compound. Impregnation with a fully dissolved solution, or solutions, of the cobalt-containing compound and the manganese-containing compound ensures good dispersion of the cobalt-containing compound and the manganese-containing compound on the support material and is thus preferred. This is in contrast, for instance, to the use of partially dissolved cobalt-containing compound and/or a partially dissolved manganese-containing compound in 'solid solutions' or suspensions, where the level of dispersion of the cobalt-containing compound and manganese-containing compound across the surface, and in the pores, of the support material can fluctuate depending on the nature of the precipitation on the support material. Furthermore, use of a fully dissolved solution, or solutions, of cobalt-containing compound and manganese-containing compound also has less of an impact upon the resulting morphology and bulk crush strength of an extrudate formed thereafter compared with solid solutions. Nevertheless, benefits of the present invention can also be realised in the case where a solid solution, or solutions, of a partially undissolved cobalt-containing compound and/or manganese-containing compound is used.

Where a powder or granulate of a support material is contacted with a solution, or solutions, of cobalt-containing compound and manganese-containing compound, the amount of solution used preferably corresponds to an amount of liquid which is suitable for achieving a mixture which is of a suitable consistency for further processing, for example for shaping by extrusion. In that case, complete removal of the solvent of the impregnating solution may be effected after formation of the shaped particle, such as an extrudate.

Suitable cobalt-containing compounds are those which are thermally decomposable to an oxide of cobalt following calcination and which are preferably completely soluble in the impregnating solution. Preferred cobalt-containing compounds are the nitrate, acetate or acetylacetonate of cobalt, most preferably the nitrate of cobalt, for example cobalt nitrate hexahydrate. It is preferred to avoid the use of the halides because these have been found to be detrimental.

Suitable manganese-containing compounds are those which are thermally decomposable following calcination and which are preferably completely soluble in the impregnating solution. Preferred manganese-containing compounds are the nitrate, acetate or acetylacetonate of manganese, most preferably the acetate of manganese.

The solvent of the impregnating solution(s) may be either an aqueous solvent or a non-aqueous, organic solvent. Suitable non-aqueous organic solvents include, for example, alcohols (e.g. methanol, ethanol and/or propanol), ketones (e.g. acetone), liquid paraffinic hydrocarbons and ethers. Alternatively, aqueous organic solvents, for example an aqueous alcoholic solvent, may be employed. Preferably, the solvent of the impregnating solution(s) is an aqueous solvent.

In preferred embodiments, the impregnation of the support material with a cobalt-containing compound and a manganese-containing compound occurs in a single step, without any intermediate drying or calcination steps to separate the loading of the different components. As the skilled person will appreciate, the cobalt-containing compound and manganese-containing compound may be applied to the support material successively or simultaneously in separate impregnation solutions or suspensions, or preferably an impregnation solution or suspension comprising both the cobalt-containing compound and the manganese-containing compound is used.

The concentration of the cobalt-containing compound and the manganese-containing compound, in the impregnating solution(s) is not particularly limited, although preferably the cobalt-containing compound and the manganese-containing compound are fully dissolved, as discussed hereinbefore. When a powder or granulate of support material is impregnated and immediately followed by an extrusion step, the amount of the impregnating solution(s) is preferably suitable for forming an extrudable paste.

In a preferred embodiment, the concentration of the impregnating solution is sufficient to afford a supported catalyst containing from 5 wt. % to 35 wt. % of cobalt, more preferably from 7.5 wt % to 25 wt % of cobalt, even more preferably from 10 to 20 wt. % of cobalt, on an elemental basis, based on the total weight of the supported synthesis catalyst.

In another preferred embodiment, the concentration of the impregnating solution is sufficient to afford a supported catalyst containing from 2.5 wt. % to 15 wt. % of manganese, preferably from 3.0 wt % to 12.5 wt % of manganese, for example from 3.0 to 10 wt. % of manganese, or even 4.0 to 8.0 wt. % of manganese, on an elemental basis, based on the total weight of the supported synthesis catalyst, following drying and calcination.

A suitable concentration of cobalt-containing compound and/or manganese-containing compound is, for example, 0.1 to 15 moles/litre.

It will be appreciated that where the support material is in powder or granulate form, once impregnated with a cobalt-containing compound and a manganese-containing compound, the impregnated support material may be extruded or formed into shaped particles at any suitable stage before or after drying and calcining.

Impregnation of the support material is usually followed by drying of the impregnating solution in order to effect precipitation of the cobalt-containing compound and the manganese-containing compound on to the support material and preferably also to remove bound solvent of the impregnating solution (e.g. water). Drying therefore does not, for instance, lead to full decomposition of the cobalt-containing compound or otherwise lead to a change in oxidation state of the cobalt-containing compound. As will be appreciated, in embodiments where an extrusion is performed, complete drying and removal of solvent (e.g. bound solvent) of the impregnating solution may occur after forming of a shaped particle, for example by extrusion. Drying is suitably conducted at temperatures from 50° C. to 150° C., preferably 75° C. to 125° C. Suitable drying times are, for example, from 5 minutes to 72 hours. Drying may suitably be conducted in a drying oven or in a box furnace, for example, under the flow of an inert gas at elevated temperature.

Where a shaped particle, such as an extrudate, is impregnated, it will be appreciated that the support may be contacted with the impregnating solution by any suitable means including, for instance, vacuum impregnation, incipient wetness or immersion in excess liquid, as mentioned hereinbefore. Where a powder or granulate of support material is impregnated, the powder or granulate may be admixed with the impregnating solution by any suitable means of which the skilled person is aware, such as by adding the powder or granulate to a container of the impregnating solution and stirring.

Where a step of forming a shaped particle, such as an extrusion step, immediately follows impregnation of a powder or granulate, the mixture of powder or granulate and impregnating solution may be further processed if it is not already in a form which is suitable for forming a shaped particle, for instance by extrusion. For instance, the mixture may be mulled to reduce the presence of larger particles that may not be readily extruded or otherwise formed into a shaped particle, or the presence of which would otherwise compromise the physical properties of the resulting shaped particle, for example an extrudate. Mulling typically involves forming a paste which is suitable for shaping, such as by extrusion. Any suitable mulling or kneading apparatus of which the skilled person is aware may be used for mulling in the context of the present invention. For example, a pestle and mortar may suitably be used in some applications or a Simpson muller may suitably be employed. Mulling is typically undertaken for a period of from 3 to 90 minutes, preferably for a period of 5 minutes to 30 minutes. Mulling may suitably be undertaken over a range of temperatures, including ambient temperatures. A preferred temperature range for mulling is from 15° C. to 50° C. Mulling may suitably be undertaken at ambient pressures. As stated hereinbefore, it will be appreciated that complete removal of bound solvent from the impregnation solution may be conducted to effect complete precipitation after forming of the shaped particle, such as by extrusion.

In embodiments where a calcination step is performed on an impregnated powder or granulate, thereby completely removing solvent of the impregnation solution, the calcined powder or granulate may also be further processed in order to form a mixture which is suitable for forming into shaped particles, for example by extruding. For instance, an extrudable paste may be formed by combining the calcined powder or granulate with a suitable solvent, for example a solvent used for impregnation, preferably an aqueous solvent, and mulled as described above.

Preparation of the supported Co—Mn Fischer-Tropsch synthesis catalyst involves a calcination step. As will be understood, calcination is required for converting the cobalt-containing compound which has been impregnated on the support material into an oxide of cobalt. Thus, calcination leads to thermal decomposition of the cobalt-containing compound, and not merely removal of bound solvent of an impregnating solution, as for instance in the case of drying.

Calcination may be performed by any method known to those of skill in the art, for instance in a fluidized bed or rotary kiln at a temperature of at least 250° C., preferably from 275° C. to 500° C. In some embodiments, calcination may be conducted as part of an integrated process where calcination and reductive activation of the synthesis catalyst to yield a reduced Fisher-Tropsch synthesis catalyst are performed in the same reactor.

In a particularly preferred embodiment, the supported Co—Mn Fischer-Tropsch synthesis catalyst used in the process of the invention is obtained or obtainable from a process comprising the steps of:

(a) impregnating a support material with: a cobalt-containing compound and a manganese-containing compound in a single impregnation step to form an impregnated support material; and (b) drying and calcining the impregnated support material to form the supported Co—Mn Fischer-Tropsch synthesis catalyst.

A particular advantage of this embodiment is the expediency with which a support material may be modified and converted into a supported Co—Mn Fischer-Tropsch synthesis catalyst using only a single impregnation step followed by a drying and calcination step. Thus, in preferred embodiments, the support material used in connection with the invention has undergone no prior modification, for instance by the addition of promoters, dispersion aids, strength aids and/or binders, or precursors thereof, before impregnation in step (a) of the process.

The supported Co—Mn Fischer-Tropsch synthesis catalyst used in the process of the present invention may additionally comprise one or more promoters, dispersion aids or binders. Promoters are typically added to promote reduction of an oxide of cobalt to cobalt metal, preferably at lower temperatures. Preferably, the one or more promoters is selected from the list consisting of ruthenium, palladium, platinum, rhodium, rhenium, chromium, nickel, iron, molybdenum, tungsten, zirconium, gallium, thorium, lanthanum, cerium and mixtures thereof. Promoter is typically used in a cobalt to promoter atomic ratio of up to 250:1 and more preferably up to 125:1, still more preferably up to 25:1, and most preferably 10:1. In preferred embodiments, the one or more promoters are present in the cobalt-containing Fischer-Tropsch synthesis catalyst obtained in an amount from 0.1 wt. % to 3 wt. %, on an elemental basis, based on the total weight of the supported synthesis catalyst.

The addition of the promoters, dispersion aids, strength aids, or binders may be integrated at several stages of the catalyst preparation process. Preferably, the promoters, dispersion aids or binders, or precursors thereof, is/are introduced during impregnation step(s) where the cobalt-containing compound and manganese-containing compound are introduced.

The supported Co—Mn Fischer-Tropsch synthesis catalyst may conveniently be converted into a reduced supported Co—Mn Fischer-Tropsch synthesis catalyst by reductive activation by any known means of which the skilled person is aware which is capable of converting cobalt oxide to the active cobalt metal. Thus, in one embodiment, the process of the invention further comprises a preceding step of reducing a Co—Mn Fischer-Tropsch synthesis catalyst to form a reduced Co—Mn Fischer-Tropsch synthesis catalyst by contacting with a hydrogen-containing gas stream. The step of forming a reduced synthesis catalyst may be carried out batch wise or continuously in a fixed bed, fluidised bed or slurry phase reactor, or in-situ in the same reactor as will be subsequently used for the Fischer-Tropsch synthesis reaction. Reduction is suitably performed at a temperature of from 150° C. to 500° C., preferably from 200° C. to 400° C., more preferably from 250° C. to 350° C.

As will be appreciated, the gaseous reactant mixture supplied to the Fischer-Tropsch reaction may also be suitable for reducing the supported Co—Mn Fischer-Tropsch synthesis catalyst to form a reduced supported Co—Mn Fischer-Tropsch synthesis catalyst in situ, without requiring any preceding or distinct reductive activation step.

In the Fischer-Tropsch reaction of the invention, a gaseous mixture of hydrogen, carbon monoxide, and carbon dioxide is supplied to the Fischer-Tropsch synthesis reaction as a reactant stream. The gaseous reactant stream may also comprise other gaseous components, such as nitrogen, water, methane and other saturated and/or unsaturated light hydrocarbons, each preferably being present at a concentration of less than 30% by volume. In some or all embodiments of the present invention, a gaseous mixture of hydrogen, carbon monoxide, carbon dioxide, and at least one or more other gaseous components, such as nitrogen, water, methane and other saturated and/or unsaturated light hydrocarbons, is supplied to the Fischer-Tropsch synthesis reaction as a reactant stream. In some or all embodiments of the present invention, a gaseous mixture consisting essentially of hydrogen, carbon monoxide, and carbon dioxide is supplied to the Fischer-Tropsch synthesis reaction as a reactant stream.

In the Fischer-Tropsch reaction of the invention, the amount of carbon dioxide present in the gaseous reactant stream is at least 5% v/v of the total gaseous feed to the Fischer-Tropsch synthesis reaction. In some or all embodiments of the present invention, the amount of carbon dioxide present in the gaseous reactant stream is at least 7.5% v/v. In some or all embodiments of the present invention, the amount of carbon dioxide present in the gaseous reactant stream is at least 10% v/v. Typically, the amount of carbon dioxide present in the gaseous reactant stream is at most 40% v/v. In some or all embodiments of the present invention, the amount of carbon dioxide present in the gaseous reactant stream is at most 30% v/v. In some or all embodiments of the present invention, the amount of carbon dioxide present in the gaseous reactant stream is at most 25% v/v. Examples of suitable amounts of carbon dioxide present in the gaseous reactant stream include the ranges: from 5% v/v to 40% v/v; from 5% v/v to 30% v/v; from 5% v/v to 25% v/v; from 7.5% v/v to 40% v/v; from 7.5% v/v to 30% v/v; from 7.5% v/v to 25% v/v; from 10% v/v to 40% v/v; from 10% v/v to 30% v/v; or from 10% v/v to 25% v/v.

In the process of the present invention, at least part of the carbon dioxide supplied to the Fischer-Tropsch synthesis reaction is consumed in the reaction. Without wishing to be bound by theory, it is believed that at least part of the carbon dioxide supplied to the Fischer-Tropsch synthesis reaction is consumed in the formation of oxygenates, in particularly in the formation of alcohols.

In the Fischer-Tropsch reaction of the invention, the volume ratio of hydrogen to carbon monoxide ($H_2$:CO) in the gaseous reactant mixture is typically at least 0.6:1, more typically at least 0.8:1. In some or all embodiments of the Fischer-Tropsch reaction of the invention, the volume ratio of hydrogen to carbon monoxide ($H_2$:CO) in the gaseous reactant mixture is at least 1:1, preferably at least 1.1:1, more preferably at least 1.2:1, more preferably at least 1.3:1, more preferably at least 1.4:1, more preferably at least 1.5:1, or even at least 1.6:1. In some or all embodiments of the present invention, the volume ratio of hydrogen to carbon monoxide ($H_2$:CO) in the gaseous reactant mixture is at most 5:1, preferably at most 3:1, most preferably at most 2.2:1. Examples of suitable volume ratios of hydrogen to carbon monoxide ($H_2$:CO) in the gaseous reactant mixture include the ranges: from 0.6:1 to 5:1; from 0.6:1 to 3:1; from 0.6:1 to 2.2:1; from 0.8:1 to 5:1; from 0.8:1 to 3:1; from 0.8:1 to 2.2:1; from 1:1 to 5:1; from 1:1 to 3:1; from 1:1 to 2.2:1; from 1.1:1 to 3:1; from 1.2:1 to 3:1; from 1.3:1 to 2.2:1; from 1.4:1 to 5:1; from 1.4:1 to 3:1; from 1.4:1 to 2.2:1; from 1.5:1 to 3:1; from 1.5:1 to 2.2:1; and, from 1.6:1 to 2.2:1.

In some or all embodiments, the volume ratio of carbon dioxide to carbon monoxide ($CO_2$:CO) in the gaseous reactant mixture is at least 0.1:1, typically at least 0.15:1, more typically at least 0.2:1, for example 0.25:1, such as 0.3:1. Examples of suitable volume ratios of carbon dioxide to carbon monoxide ($CO_2$:CO) in the gaseous reactant mixture include the ranges: from 0.1:1 to 3:1; from 0.1:1 to 2:1; from 0.1:1 to 1.5:1; from 0.1:1 to 1.3:1; from 0.15:1 to 3:1; from 0.15:1 to 2:1; from 0.15:1 to 1.5:1; from 0.15:1 to 1.3:1; from 0.2:1 to 3:1; from 0.2:1 to 2:1; from 0.2:1 to 1.5:1; from 0.2:1 to 1.3:1; from 0.25:1 to 3:1; from 0.25:1 to 2:1; from 0.25:1 to 1.5:1; from 0.25:1 to 1.3:1; from 0.3:1 to 3:1; from 0.3:1 to 2:1; from 0.3:1 to 1.5:1; and, from 0.3:1 to 1.3:1.

In some or all embodiments, the volume ratio of carbon dioxide to hydrogen ($CO_2$:$H_2$) in the gaseous reactant mixture is at least 0.01:1, typically at least 0.05:1, more typically at least 0.1:1, for example 0.15:1, such as 0.2:1. Examples of suitable volume ratios of carbon dioxide to hydrogen ($CO_2$:$H_2$) in the gaseous reactant mixture include the ranges: from 0.01:1 to 3:1; from 0.01:1 to 1.5:1; from 0.01:1 to 1:1; from 0.01:1 to 0.7:1; from 0.05:1 to 3:1; from 0.05:1 to 1.5:1; from 0.05:1 to 1:1; from 0.05:1 to 0.7:1; from 0.1:1 to 3:1; from 0.1:1 to 1.5:1; from 0.1:1 to 1:1; from 0.1:1 to 0.7:1; from 0.15:1 to 3:1; from 0.15:1 to 1.5:1; from 0.15:1 to 1:1; from 0.15:1 to 0.7:1; from 0.2:1 to 3:1; from 0.2:1 to 1.5:1; from 0.2:1 to 1:1; and, from 0.2:1 to 0.7:1.

As discussed hereinbefore, the Fischer-Tropsch synthesis process of the present invention has been surprisingly found to afford a Fischer-Tropsch catalyst exhibiting high selectivity for oxygenates, in particularly alcohols; the Fischer-Tropsch synthesis process of the present invention has also been surprisingly found to afford a Fischer-Tropsch catalyst exhibiting high selectivity for olefins. Furthermore, at least in some embodiments, the catalytic activity has also been found to be superior.

Conventional Fischer-Tropsch temperatures may be used in order to prepare alcohols and liquid hydrocarbons in accordance with the present invention. For example, the temperature of the reaction may suitable be in the range from 100 to 400° C., such as from 150 to 350° C., or from 150 to 250° C. The pressure of the reaction may suitably be in the range from 1 to 120 bar (from 1 to 10 MPa), such as from 5 to 100 bar (from 0.5 to 10 MPa), from 5 to 75 bar (from 0.5 to 7.5 MPa), from 15 to 75 bar (from 1.5 to 7.5 MPa), from 10 to 50 bar (from 1.5 to 5 MPa), or from 20 to 50 bar (from 2.0 to 5.0 MPa).

In preferred embodiments, the temperature of the Fischer-Tropsch reaction is in the range from 150 to 350° C., more preferably from 180 to 300° C., and most preferably from 200 to 260° C. In preferred embodiments, the pressure of the Fischer-Tropsch reaction is in the range from 1 to 120 bar (from 0.1 to 10.2 MPa), such as from 5 to 100 bar (from 0.5 to 10 MPa), from 10 to 100 bar (from 1 to 10 MPa), more preferably from 10 to 60 bar (from 1 to 6 MPa) and most preferably from 20 to 45 bar (from 2 to 4.5 MPa).

The Fischer-Tropsch synthesis reaction may be performed in any suitable type of reactor, for example it may be performed in a fixed bed reactor, a slurry bed reactor, or a CANs reactor.

In another aspect of the present invention, there is provided the use of carbon dioxide in the feed to a Fischer-Tropsch synthesis reaction using a supported Co—Mn Fischer-Tropsch synthesis catalyst, wherein the supported synthesis catalyst comprises at least 2.5 wt % of manganese, on an elemental basis, based on the total weight of the supported synthesis catalyst; the weight ratio of manganese to cobalt, on an elemental basis, is 0.2 or greater, for increasing the selectivity of the Fischer-Tropsch process for the production of alcohols.

The invention will now be further described by reference to the following Examples which are illustrative only. In the Examples, CO conversion is defined as moles of CO used/moles of CO fed×100 and carbon selectivity as moles of CO attributed to a particular product/moles of CO converted× 100. Unless otherwise stated, temperatures referred to in the Examples are applied temperatures and not catalyst/bed temperatures. Unless otherwise stated, pressures referred to in the Examples are absolute pressures.

EXAMPLES

Example 1—Catalyst Preparation

An amount of $Co(NO_3)_2 \cdot 6H_2O$ and an amount of $Mn(OAc)_2 \cdot 4H_2O$ were mixed in a solution with a small amount of water. This mixture was then added slowly to 100 g P25 $TiO_2$ powder and mixed to obtain a homogeneous mixture. $Co(NO_3)_2 \cdot 6H_2O$ was used in an amount so as to give approximately 10 wt. % elemental Co on $TiO_2$. The resultant paste/dough was extruded to form extrudate pellets and then dried and calcined at 300° C. Characterization was complete on the resulting catalysts using X-ray diffraction, $H_2$ chemisorption, elemental analysis, temperature programmed reduction and BET surface area techniques.

Several catalysts were made with between 55 and 62 g of cobalt hydrate hexahydrate, and between 0 and 55 g of manganese acetate tetrahydrate to give different manganese loadings and different Mn:Co ratios as detailed in Table 1.

TABLE 1

| Mass of cobalt nitrate hexahydrate (g) | Cobalt loading (wt. %) | Mass of manganese acetate tetrahydrate (g) | Manganese Loading (wt. %) | Mn/Co ratio |
|---|---|---|---|---|
| 62 | 10 | 55 | 10 | 1.00 |
| 60 | 10 | 40 | 7.5 | 0.75 |
| 58 | 10 | 25 | 5 | 0.50 |
| 57 | 10 | 16.2 | 3 | 0.30 |
| 56 | 10 | 10.8 | 2 | 0.20 |
| 56 | 10 | 7.6 | 1.5 | 0.15 |
| 56 | 10 | 5.4 | 1 | 0.10 |
| 55 | 10 | 0 | 0 | 0.00 |

Example 2—General Procedure for Fischer-Tropsch Synthesis 1 ml samples of catalyst in the form of extrudates (1.25-3.5 mm) were loaded into a high throughput parallel reactor and reduced under a $H_2$ stream (15 h, at 300° C., 100% $H_2$, atmospheric pressure). The gaseous supply was switched to a mixture of hydrogen and carbon monoxide ($H_2/C_{O=1.8}$), additionally comprising 10% v/v nitrogen and 8% v/v carbon dioxide, the pressure was maintained at 4.3 MPa absolute, and a GHSV of 1500 hr-1. The temperature was raised to achieve conversion of 55-65% based on CO, and maintained throughout the Fischer-Tropsch reaction. On line analytics were completed by GC. Results are presented in Tables 2 and 3 below.

TABLE 2

| Selectivity % | 10% Co/TiO$_2$ | 1% Mn/10% Co/TiO$_2$ | 5% Mn/10% Co/TiO$_2$ |
|---|---|---|---|
| Methanol | 0.25 | 0.27 | 0.7 |
| Ethanol | 0.00 | 0 | 0.06 |
| Propanol | 0.07 | 0.15 | 0.83 |
| Butanol | 0.00 | 0 | 2.73 |
| Pentanol | 0.08 | 0.19 | 2.42 |
| Hexanol | 0.06 | 0.16 | 1.97 |
| Heptanol | 0.06 | 0.14 | 1.57 |
| Octanol | 0.05 | 0.13 | 1.21 |
| Nonanol | 0.05 | 0.12 | 0.96 |
| Decanol | 0.05 | 0.1 | 0.75 |
| CO$_2$ conversion (%) | 10.90 | 24.60 | 26.1 |
| Applied Temperature (C) | 198 | 197 | 203 |
| Total OH selectivity (%) | 0.70 | 1.60 | 14.8 |
| Total Olefin selectivity (%) | 4.2 | 5.6 | 20.9 |

The results presented in Table 2 shows that the 10% Co/5% Mn/TiO$_2$ catalyst has approximately a 20-30 fold increase in alcohols over the non-manganese catalyst.

TABLE 3

| Molar rate: | 0% Mn/10% Co/TiO$_2$ | 1% Mn/10% Co/TiO$_2$ | 5% Mn/10% Co/TiO$_2$ |
|---|---|---|---|
| RM_(Methanol) [mol/h] | 2.271E−05 | 2.537E−05 | 6.119E−05 |
| RM_(Ethanol) [mol/h] | 0 | 0 | 2.846E−06 |
| RM_(Propanol) [mol/h] | 2.272E−06 | 4.719E−06 | 2.43E−05 |
| RM_(Butanol) [mol/h] | 1.754E−06 | 4.384E−06 | 5.879E−05 |
| RM_(1-Pentanol) [mol/h] | 1.558E−06 | 3.604E−06 | 4.159E−05 |
| RM_(1-Hexanol) [mol/h] | 9.817E−07 | 2.747E−06 | 2.896E−05 |
| RM_(1-Heptanol) [mol/h] | 7.563E−07 | 2.004E−06 | 2.005E−05 |
| RM_(1-Octanol) [mol/h] | 6.144E−07 | 1.537E−06 | 1.322E−05 |
| RM_(1-Nonanol) [mol/h] | 5.237E−07 | 1.253E−06 | 8.78E−06 |
| RM_(1-Decanol) [mol/h] | 3.595E−07 | 9.917E−07 | 6.438E−06 |
| RM_(1-Undecanol) [mol/h] | 2.829E−07 | 6.378E−07 | 4.4E−06 |
| RM_(1-Dodecanol) [mol/h] | 2.753E−07 | 4.78E−07 | 2.811E−06 |
| RM_(1-Tridecanol) [mol/h] | 0.0 | 3.209E−07 | 1.946E−06 |
| RM_(1-Tetradecanol) [mol/h] | 0 | 0 | 1.154E−06 |

Table 3 shows the molar rates of products produced under the CO$_2$-containing feed, in particularly for the longer-chain linear alcohols

The invention claimed is:

1. A process for the preparation of a composition comprising oxygenates and hydrocarbons by means of a Fischer-Tropsch synthesis reaction, said process comprising contacting a mixture of hydrogen, carbon monoxide, and carbon dioxide gases with a supported Co—Mn Fischer-Tropsch synthesis catalyst, wherein the supported synthesis catalyst comprises at least 2.5 wt % of manganese, on an elemental basis, based on the total weight of the supported synthesis catalyst; the weight ratio of manganese to cobalt, on an elemental basis, is 0.2 or greater; and, wherein the amount of carbon dioxide present in the Fischer-Tropsch synthesis reaction is at least 5% v/v.

2. A process according to claim 1, wherein, of the compounds in the composition comprising oxygenates and hydrocarbons having carbon chain length of eight carbon atoms or more, at least 30 wt. % are oxygenates.

3. A process according to claim 1, wherein at least 50 wt. % of the oxygenates in the composition comprising oxygenates and hydrocarbons are alcohols.

4. A process according to claim 1, wherein the amount of carbon dioxide present in the Fischer-Tropsch synthesis reaction is at least 10% v/v.

5. A process according to claim 1, wherein the amount of carbon dioxide present in the Fischer-Tropsch synthesis reaction is in the range of from 5% v/v to 25% v/v.

6. A process according to claim 1, wherein the support material of the supported Co—Mn Fischer-Tropsch synthesis catalyst comprises a material selected from titania, zinc oxide, zirconia, and ceria.

7. A process according to claim 1, wherein the support material comprises titania.

8. Process according to claim 7, wherein the support material is titania.

9. A process according to claim 1, wherein the weight ratio of manganese to cobalt present in the supported Co—Mn Fischer-Tropsch synthesis catalyst, on an elemental basis, is in the range of from 0.2 to 3.0.

10. A process according to claim 1, wherein the supported Co—Mn Fischer-Tropsch synthesis catalyst contains from 5 wt. % to 35 wt. % of cobalt, on an elemental basis, based on the total weight of the supported synthesis catalyst.

11. A process according to claim 1, wherein the supported Co—Mn Fischer-Tropsch synthesis catalyst contains from 2.5 wt. % to 15 wt. % of manganese, on an elemental basis, based on the total weight of the supported synthesis catalyst.

12. A process according to claim 1, wherein the combined amount of cobalt and manganese in the supported Co—Mn Fischer-Tropsch synthesis catalyst is less than 30 wt. %, on an elemental basis, based on the total weight of the supported synthesis catalyst.

13. A process according to claim 1, wherein the molar ratio of hydrogen to carbon monoxide is at least 1.

14. A process according to claim 1, wherein the Fischer-Tropsch synthesis reaction is conducted at a temperature of less than or equal to 300° C.

15. A process according to claim 1, wherein the Fischer-Tropsch synthesis reaction is conducted at a pressure in the range of from 1.0 to 10.0 MPa absolute.

16. A process according to claim 1, wherein the supported Co—Mn Fischer-Tropsch synthesis catalyst comprises less than 0.1 wt % of copper.

17. A process according to claim 1, wherein the composition comprising oxygenates and hydrocarbons comprises at least 1 wt % olefins.

18. A process according to claim 1, wherein the composition comprising oxygenates and hydrocarbons comprises linear alpha olefins.

19. A process according to claim 1, wherein the support material is titanic, and
wherein the supported Co—Mn Fischer-Tropsch synthesis catalyst contains from 2.5 wt. % to 15 wt. % of manganese, on an elemental basis, based on the total weight of the supported synthesis catalyst, and
wherein the weight ratio of manganese to cobalt present in the supported Co—Mn Fischer-Tropsch synthesis catalyst, on an elemental basis, is in the range of from 0.2 to 3.0.

20. A process for the preparation of a product composition comprising oxygenates and hydrocarbons via a Fischer-Tropsch synthesis reaction, said process comprising contacting a mixture of hydrogen, carbon monoxide, and carbon dioxide gases with a supported Co—Mn Fischer-Tropsch synthesis catalyst, to produce the product composition, wherein
the supported synthesis catalyst comprises at least 2.5 wt % of manganese, on an elemental basis, based on the total weight of the supported synthesis catalyst;
the weight ratio of manganese to cobalt, on an elemental basis, is 0.2 or greater;
the amount of carbon dioxide present in the Fischer-Tropsch synthesis reaction is at least 5% v/v; and at least 30 wt. % of compounds in the product composition having a carbon chain length of eight carbon atoms or more are oxygenates; and at least 50 wt. % of the oxygenates of the product composition are alcohols.

21. A process according to claim 20, wherein the amount of carbon dioxide present in the Fischer-Tropsch synthesis reaction is at least 10% v/v.

* * * * *